(12) United States Patent
Holmqvist et al.

(10) Patent No.: US 9,011,375 B2
(45) Date of Patent: Apr. 21, 2015

(54) MEDICAMENT DELIVERY DEVICE

(75) Inventors: Anders Holmqvist, Värmdö (SE); Sebastian Karlsson, Sundbyberg (SE)

(73) Assignee: SHL Group AB, Nacka Strand (SE)

( * ) Notice: Subject to any disclaimer, the term of this patent is extended or adjusted under 35 U.S.C. 154(b) by 165 days.

(21) Appl. No.: 13/819,529

(22) PCT Filed: Aug. 23, 2011

(86) PCT No.: PCT/SE2011/051011
§ 371 (c)(1),
(2), (4) Date: Mar. 11, 2013

(87) PCT Pub. No.: WO2012/030276
PCT Pub. Date: Mar. 8, 2012

(65) Prior Publication Data
US 2013/0218074 A1    Aug. 22, 2013

Related U.S. Application Data

(60) Provisional application No. 61/378,603, filed on Aug. 31, 2010, provisional application No. 61/380,289, filed on Sep. 6, 2010.

(30) Foreign Application Priority Data

Aug. 31, 2010  (SE) ...................................... 1050897
Sep. 6, 2010   (SE) ...................................... 1050911

(51) Int. Cl.
*A61M 5/20*     (2006.01)
*A61M 5/315*    (2006.01)
(Continued)

(52) U.S. Cl.
CPC ......... *A61M 5/31515* (2013.01); *A61M 5/2033* (2013.01); *A61M 5/24* (2013.01); *A61M 5/28* (2013.01); *A61M 5/31511* (2013.01)

(58) Field of Classification Search
CPC ..................... A61M 5/31571; A61M 5/31596; A61M 5/3146; A61M 5/2066; A61M 5/2448; A61M 5/2033; A61M 2005/2073; A61M 2005/202; A61M 5/31515; A61M 5/31511; A61M 5/24; A61M 5/28
USPC .......................................................... 604/135
See application file for complete search history.

(56) References Cited

U.S. PATENT DOCUMENTS 4,755,169 A   7/1988   Sarnoff et al.
6,319,225 B1  11/2001  Sugita et al.
(Continued)

FOREIGN PATENT DOCUMENTS

WO       00/62839 A2    10/2000
WO     2004/004809 A1    1/2004
(Continued)

OTHER PUBLICATIONS

Swedish Patent Office, Int'l Search Report in PCT/SE2011/051011, Dec. 1, 2011.
(Continued)

*Primary Examiner* — Manuel Mendez
(74) *Attorney, Agent, or Firm* — Piedmont Intellectual Property (57) ABSTRACT

A medicament delivery device includes a housing; a drive force mechanism slidable in the housing's distal part; a member connected to the drive force mechanism for holding it in a loaded state and axially movable in relation to the distal part a predetermined distance by the housing's proximal part when the parts are moved toward each other; and an actuation member to be biased in relation to the distal part from a non-operating position partially protruding from the distal part to an operating position confined within the distal part. The actuation member can release the drive force mechanism from its loaded state, and is resiliently connected to the distal part such that it is always recoiled after being biased regardless of whether the actuation mechanism is released. The drive force mechanism is released only after the holding member moves and the actuation member is biased from non-operating to operating position.

18 Claims, 8 Drawing Sheets

(51) Int. Cl.
*A61M 5/24* (2006.01)
*A61M 5/28* (2006.01)

(56) References Cited

U.S. PATENT DOCUMENTS

| | | |
|---|---|---|
| 6,793,646 B1 | 9/2004 | Giambattista et al. |
| 6,893,420 B2 | 5/2005 | Arnisolle |
| 8,372,031 B2 | 2/2013 | Elmen et al. |

FOREIGN PATENT DOCUMENTS

| | | |
|---|---|---|
| WO | 2007/115424 A1 | 10/2007 |
| WO | 2009/147026 A1 | 12/2009 |
| WO | 2010/033882 A1 | 3/2010 |
| WO | 2012/030277 A1 | 3/2012 |

OTHER PUBLICATIONS

Swedish Patent Office, Written Opinion in PCT/SE2011/051011, Dec. 1, 2011.

MEDICAMENT DELIVERY DEVICE

This application is a national stage entry of PCT/SE2011/051011, which claims priority from U.S. Provisional Applications No. 61/378,603 and No. 61/380,289.

TECHNICAL FIELD

The present invention relates to a medicament delivery device for administering, dispensing or delivering medicaments in a safe and reliable way. More particularly, it relates to an injection device for manually penetrating a needle arranged to said device and automatically injecting a drug mixture from a multiple chamber container

BACKGROUND OF THE INVENTION

There are different types of medicaments that can be stored for a long time and that are filled in containers e.g. cartridges, syringes, ampoules, canisters or the like, containing a ready-to-use medicament in liquid state. However, there are also other types of medicaments that are a mixture of two substances, a medicament agent (e.g. lyophilized, powdered or concentrated liquid) and a diluent (e.g. water, dextrox solution or saline solution), wherein these types of medicaments cannot be pre-mixed and stored for a long time because the medicament agent is unstable and can be degraded and loses its effect quickly. Hence, a user, e.g. a patient himself/herself, a physician, a nurse, hospital personnel or trained persons, has/have to perform the mixing within a limited time period prior to the delivery of a dose of medicament to a patient. Further, some medicament agents are subject to meet significant chemical changes while mixing. Such sensitive medicament agents require a particular treatment so that, when mixing said medicament agents with a diluent, unreasonable mixing force will degrade said medicament agents.

In order to facilitate the mixing, a number of containers for mixing have been developed comprising at least two chambers, known as multi-chamber containers. These multi-chambered containers comprise a first chamber containing the medicament agent and at least a second chamber containing the diluent. These chambers are sealed off with stoppers such/so that the medicament agents do not become degraded. When the medicament agent is to be mixed shortly before administering, redirecting passages are opened between the chambers, usually by depressing a distal stopper and in turn a divider stopper of the container somewhat.

The passages allow the mixing of the medicament agent and the diluent and the medicament is ready for delivery.

The above mentioned requirements can be achieved by simple medicament delivery devices, such as a common hypodermic syringe, but the procedure is of course rather awkward, in particular for users not used to handle these devices. In order to facilitate for the patients themselves to administer the medicament with a predetermined dose in an easy, safe and reliable way and also to facilitate the administration of medicaments for hospital personnel in the same facilitated way, a number of automatic and semi-automatic devices have been developed in combination with these multiple-chamber solutions for obtaining a mixing before delivery.

A self-injection device arranged with a dual-chamber container, wherein both the mixing and the injection are done automatically by mechanical means, as springs and other means, is disclosed in U.S. Pat. No. 4,755,169. A similar solution is disclosed in U.S. Pat. No. 6,793,646 wherein the mixing of a dual-chamber cartridge is done automatically by springs upon activation of the device and the injection is done by manually applying a force to a plunger rod forwardly. A drawback with these devices is that the mixing force, to which medicament agents are subject to, is too high at the beginning due to Hookes law. Hence, the medicament agents can be degraded.

Another solution is disclosed in WO 2004004809, wherein both the mixing and the injection are done automatically by electronically controlled means. A drawback with this device is that the electronics are dependent on batteries and is very sensitive to noise, moisture, water, etc.; which can result in malfunctions. Also the manufacture of these devices is more expensive than the manufacture of mechanical devices.

In U.S. Pat. No. 6,319,225 the mixing of a dual-chamber ampoule is done manually. The device is set to be vertical on a flat plane and then a downward press on its proximal case causes a relative upward movement of its plunger rod pressing a stopper of the ampoule with eye observation on actions inside the ampoule, such that a mixing is obtained. Though in U.S. Pat. No. 6,319,225 is disclosed that the best suitable process for mixing a medicament agent with a diluent, is by performing manual control of the diluent flow with adequate slowness which will be monitored by eye observation; a drawback with this device is that the mixing force, to which medicament agents are subject to, can be high if the user is stressed and wants to use the device as soon as possible. Hence, the medicament agents can be degraded.

Moreover, the handling and safety aspects of injector devices, having a certain degree of automatic functions, as well as immediate accessibility in emergency situations are issues that attract a lot of attention when developing this type of devices.

One important safety aspect when handling an auto-injector which is used to achieve a manual mixing and an automatic injection, is the locking of the injection means, e.g. a compressed spring arranged to drive a plunger rod, before the manual mixing has been completed.

One such device is disclosed in U.S. Pat. No. 6,893,420 wherein a self-injection device is arranged with a dual-chamber body. The mixing is done manually by a screw-tightening operation and the device comprises locking means for locking a latch means that prevent the automatic penetration and injection means from being released before the mixing has been completely finished. However, this solution is rather bulky and relies also on many components acting in co-operation and in sequence, one triggering another, which may lead to a mal-function, mal-dose accuracy, or that the device becomes complicated, hence not user friendly. This device suffers from the drawback that locking means has to be actively removed from the device after the mixing has been finished. This is a step which is not intuitive for a user, who will try to push the locking means instead of removing them. Another drawback is the dose accuracy, since the penetration starts pushing the stoppers, the medicament will be expelled during the whole penetration sequence, leading to so called wet injections and delivery of medicament through the whole penetration sequence instead of injecting the required dose at the intended penetration depth.

Another such a device is disclosed in WO2007/115424A1 which relates to an injection device having a container holder having a multi-chamber container within, which is manually movable relative to the injection device for the purpose of mixing the components within the multi-chamber container. The device further comprises a spring which can bear on a part of the injection device, and a coupling element for coupling the container holder to the spring such that, during the movement of the container holder into the injection device, the spring is tensioned. The device also comprises an activation knob and a push button, wherein the activation knob has to be rotated for forcing the push button to protrude from the housing and thereby setting the device in a ready for injection delivery state. However, this solution suffers from the drawback that the activation knob has to be actively manipulated for releasing the push button after the mixing has been finished. This is a step which is not intuitive for a user, who will try to find where the push button or activation means are located instead of rotating the knob.

Moreover, another device disclosed in WO2009/147026A1, which is an earlier patent application of the present applicant, suffers from the problem of not indicating to the user when the auto-injection has started and also when the auto-injection is finished.

Even though the devices according to U.S. Pat. No. 6,893,420, WO2007/115424A and WO2009/147026A1 have proved to function well and display a degree of safety, there is always a desire for improvements of such devices, among them being the design of the mechanism in order to simplify the manufacture and assembly in order to reduce costs but at the same time having improved features maintaining or even improving the reliability of the safety and function of the device.

BRIEF DESCRIPTION OF THE INVENTION

The aim of the present invention is to provide an improved medicament delivery device capable of handling medicament delivery in a safe and reliable way wherein the risk of accidental premature firing of the device is precluded or minimised.

This aim is obtained according to a main aspect of the invention by a medicament delivery device according to the independent patent claims. Preferable details of the technical and/or functional features of the invention form the subject of the dependent patent claims.

According to a main aspect of the invention, it is characterised by a medicament delivery device comprising a generally elongated housing, which housing comprises a proximal housing part and a distal housing part arranged and mounted to be movable relative each other; a drive force mechanism accommodated in said distal housing part and being slidably arranged in relation to the distal housing part; a container filled with medicament arranged within said proximal housing part; a holding member operably connected to said drive force mechanism for holding said drive force mechanism in a loaded state, wherein said holding member is arranged to be axially moved in relation to the distal housing part a predetermined distance towards a distal end of the device by the proximal housing part when said housing parts are moved towards each other; and an actuation member configured to be biased in relation to the distal housing part from a non-operating position in which the actuation member partially protrudes from the distal housing part to an operating position in which the actuation member is confined within the distal housing, and wherein said actuation member is operably connected to said drive force mechanism for releasing the drive force mechanism from its loaded state; wherein said actuation member is resiliently connected to the distal housing part such that said actuation member is always recoiled after being biased regardless of whether the actuation mechanism is released; and wherein said drive force mechanism is configured to be released from its loaded state only after the holding member is axially moved in relation to the distal housing part and the actuation member is biased from the non-operating to the operating position.

According to another aspect of the invention, the proximal housing part comprises a co-acting means and the holding member comprises a counter co-acting means which interact together for moving the holding member in relation to the distal housing part a predetermined distance towards the distal end of the device. Further, the drive force mechanism comprises a plunger rod, a drive force spring and a drive member.

According to yet another aspect of the invention, the actuation member comprises engagement means and the plunger rod comprises counter engagement means which interact together and wherein said engagement means and said counter engagement means are configured such that the plunger axially moved a predetermined distance in relation to the distal housing part when said actuation member is biased.

According to a further aspect of the invention, the drive member comprises releasable means and the plunger rod comprises counter releasable means which interact together for releasably engaging the plunger rod to the drive member.

According to another aspect of the invention, the engagement means are proximally extending tongues and wherein the counter engagements means is a distal end annular surface of the plunger rod.

According to yet another aspect of the invention, the releasable means of the drive member are radially flexing arms provided with inwardly extending ledges and the counter releasable means of the plunger rod is a groove on its circumferential outer surface, wherein the inwardly extending ledges fit into said groove, and wherein the holding member is arranged completely surrounding the radially flexing arms when said holding member is in an inactive position.

According to another aspect of the invention, holding member is arranged be axially moved in relation to the distal housing part a predetermined distance towards a distal end of the device from the inactive position to the active position in which the holding member partially surrounds the radially flexing arms.

According to a further aspect of the invention, the container may be a multi-chamber medicament container and whereby the multi-chamber can be mixed by moving said housing parts in towards each other and wherein the active position of the holding member corresponds to a position of the multi-chamber, in which the multi-chamber is mixed.

There are a number of advantages with the medicament delivery device according to the present invention. The fact that the actuation member which is operably connected to the drive mechanism, i.e. directly connected to the plunger rod, cannot release the drive force mechanism from its loaded state when the two housing parts are in an initial position relative each other ensures that the device cannot be activated accidentally, i.e. it requires an active action by a user in order to active the device. The activation is initialized by moving the housing parts towards each other. According to an aspect of the invention this activation is performed by rotating the housing parts in relation to each other, which is an intuitive operation. Preferably the housing parts are threadedly connected to each other whereby one housing part is moved into the other.

During the movement of the housing parts, the drive force mechanism cannot be released and thus no delivery of medicament may be performed. Only after the two housing parts have reached a predetermined position, the drive force mechanism can be released, whereby it is possible to perform a dose delivery from the medicament container. In that respect, preferably the medicament container is a multi-chamber container, whereby the activation, i.e. moving of the housing parts, causes a distal stopper of the multi-chamber container to be pressed against the proximal end of the plunge rod wherein a mixing is performed. Thus, said actuation member is always recoiled after being biased regardless of whether the actuation mechanism is released.

In all a simple and reliable device capable of handling also multi-chamber medicament containers is obtained.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

The present invention relates to a medicament delivery device comprising a housing, more preferably a generally elongated housing extending along a longitudinal axis of the device, which housing comprises a proximal housing part 12 and a distal housing part 10 arranged and mounted to be movable relative each other along the longitudinal axis of the device; a drive force mechanism accommodated in said distal housing part and being slidably arranged in relation to the distal housing part; a container 22 filled with medicament arranged within said proximal housing part; a holding member 50 operably connected to said drive force mechanism for holding said drive force mechanism in a loaded state and arranged to be axially moved in relation to the distal housing part a predetermined distance towards a distal end of the device by the proximal housing part when said housing parts are moved towards each other along the longitudinal axis of the device; an actuation member 56 configured to be biased in relation to the distal housing part from a non-operating position in which the actuation member partially protrudes from the distal housing part to an operating position in which the actuation member is confined within the distal housing, and operably connected to said drive force mechanism for releasing the drive force mechanism from its loaded state; wherein said actuation member is resiliently connected to the distal housing part such that said actuation member is always recoiled after being biased regardless of whether the actuation mechanism is released; and wherein said drive force mechanism is configured to be released from its loaded state only after the holding member is axially moved in relation to the distal housing part and the actuation member is biased from the non-operating to the operating position.

In the present invention, the proximal housing part 12 comprises a co-acting means 60 and the holding member 50 comprises a counter co-acting means 62 which interact together for moving the holding member in relation to the distal housing part a predetermined distance towards a distal end of the device. Further, the drive force mechanism comprises a plunger rod 32, a drive force spring 34 and a drive member 40. The actuation member 56 comprises engagement means 52 and the plunger rod comprises counter engagement means 33 which interact together and wherein said engagement means and said counter engagement means are configured such that the plunger rod is axially moved a predetermined distance in relation to the distal housing part when said actuation member is biased. The drive member 40 comprises releasable means 44 and the plunger rod 32 comprises counter releasable means 42 which interact together for releasably engaging the plunger rod to the drive member.

In the present invention the container may be a multi-chamber medicament container and whereby the multi-chamber can be mixed by moving said housing parts towards each other along the longitudinal axis of the device.

The FIGS. 1-8 show an exemplary embodiment of the present invention.

Figure 1:
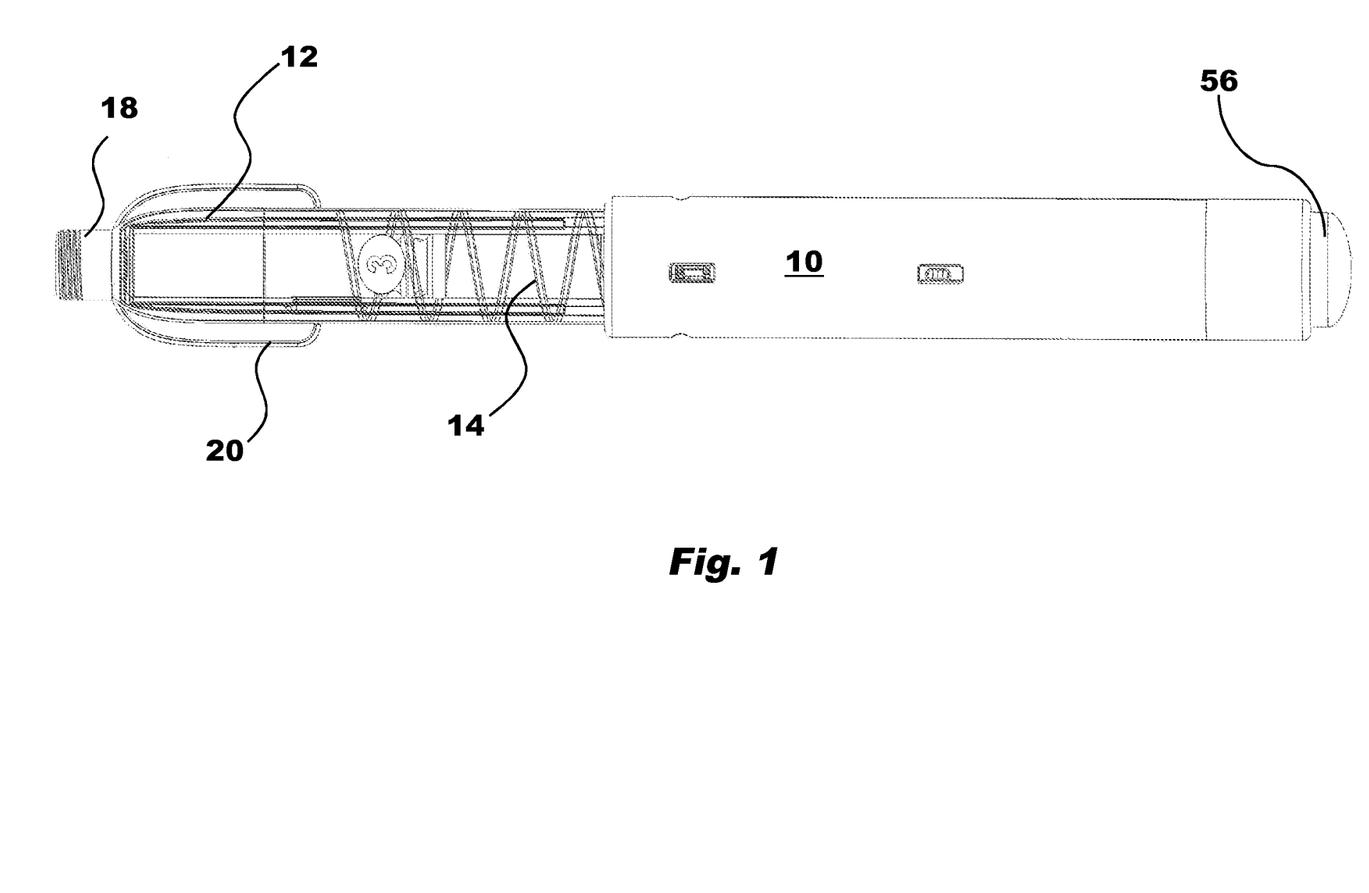
FIG. 1 is a side view of an embodiment of the invention in an initial position.

The elongated tubular housing in the exemplary embodiment, FIG. 1, comprises a distal housing part 10 and a proximal housing part 12, wherein said proximal housing part is arranged to accommodate a container 22 as a multi-chamber medicament container and whereby the components within the multi-chamber medicament container can be mixed by moving said housing parts towards each other along the longitudinal axis of the device, preferably by screwing said housing parts. In the exemplary embodiment, the outer surface of the proximal housing part 12 comprises threads 14 arranged to cooperate with corresponding threads 16 on the inner surface of the distal housing part 10. The proximal end of the proximal housing part is further arranged with a neck portion 18, which neck portion 18 is arranged with attachment means for attaching a medicament delivery member (not shown), wherein the medicament delivery member is preferably an injection needle. It is however to be understood that other types of medicament delivery members may be employed such as mouth or nose pieces, nozzles, nebulizing units etc. The proximal housing part 12 is also arranged with turning members 20 such as longitudinally extending wings, which facilitate the manual turning of the proximal housing part in relation to the distal housing part. Further, the inner surface of the distal housing part comprises a circumferential ledge.

Figure 2:
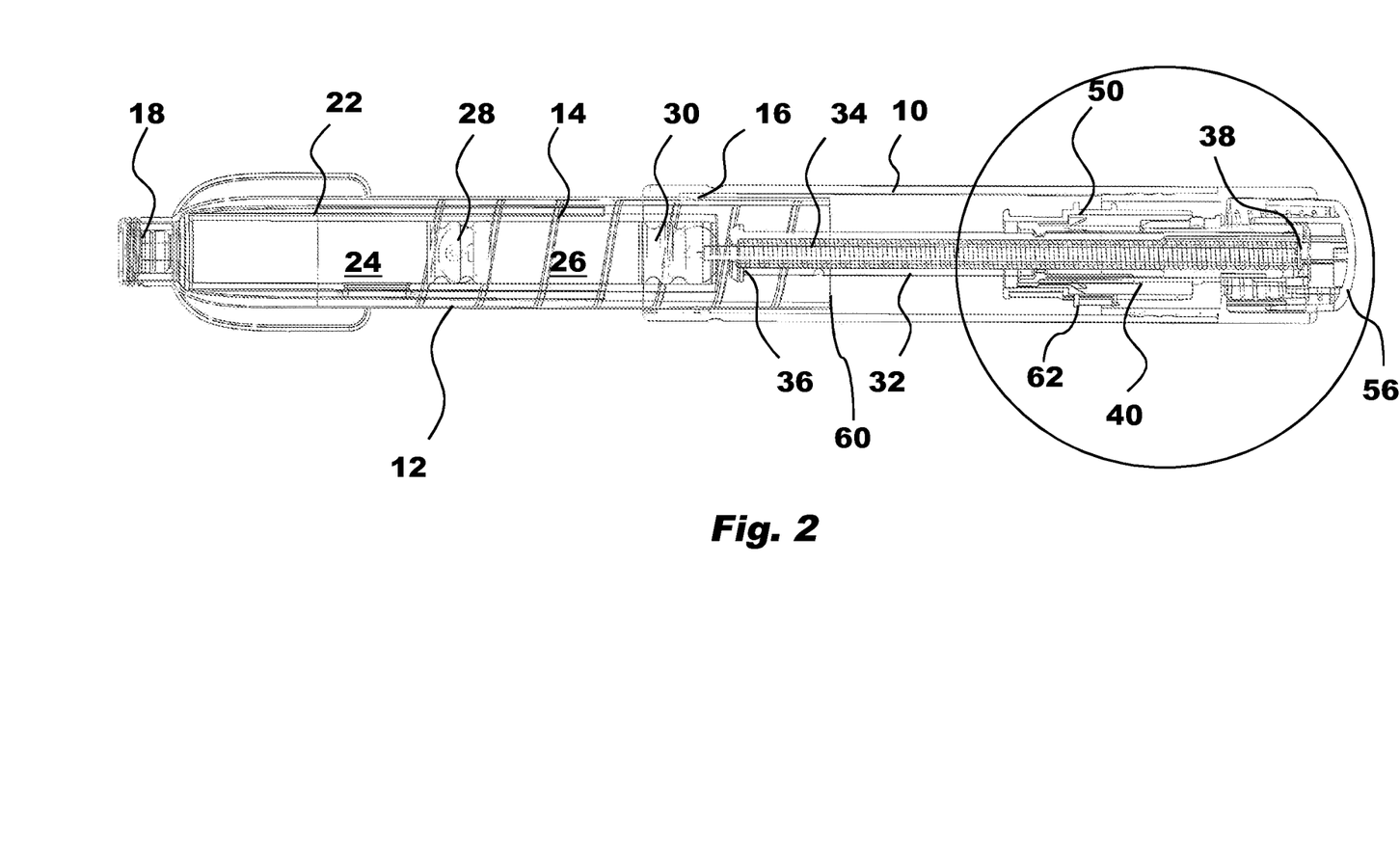
FIG. 2 is a cross-sectional side view of the device of FIG. 1.
Figure 3:
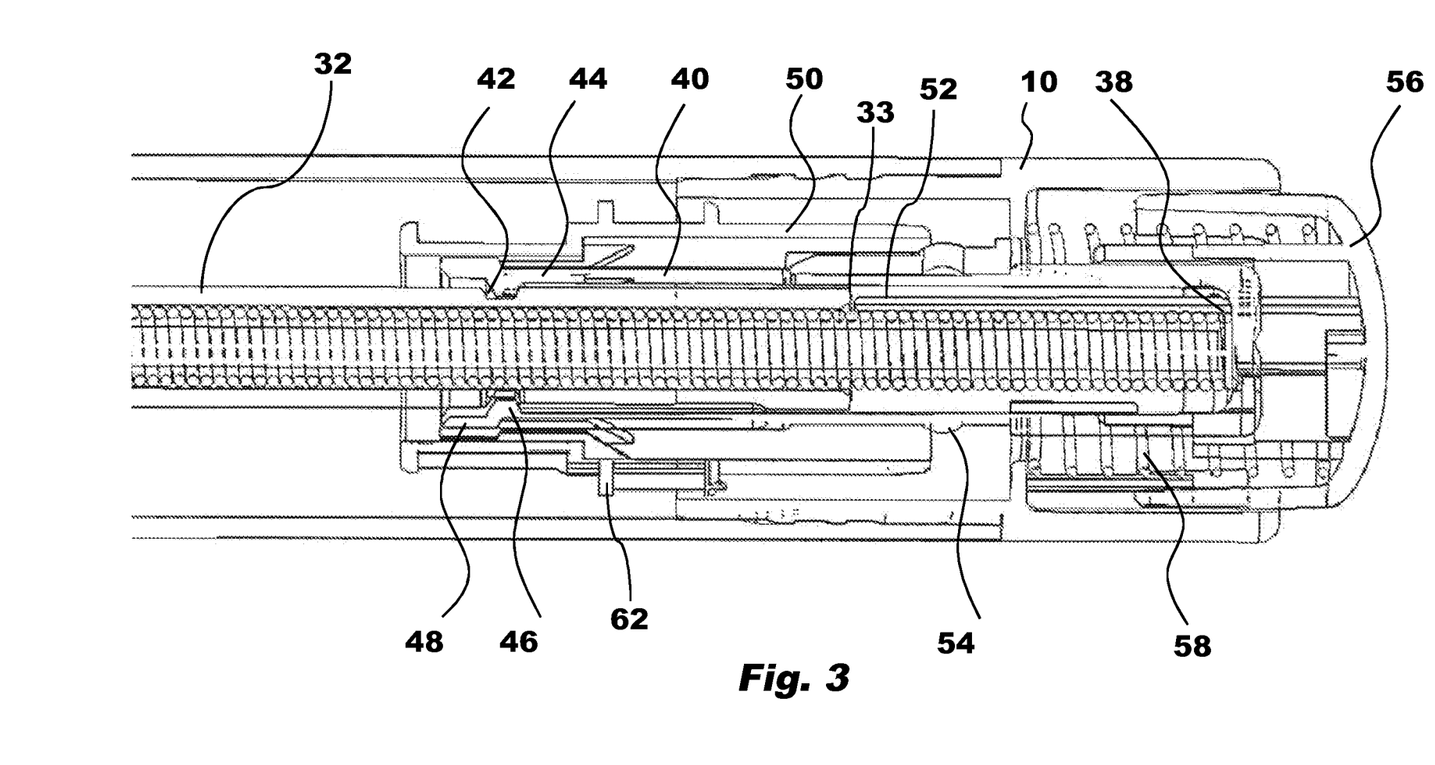
FIG. 3 is a detailed view taken from the area III of FIG. 2, and FIGS. 4 to 8 are cross-sectional views of the device of FIG. 1 in different functional positions.
Figure 4:
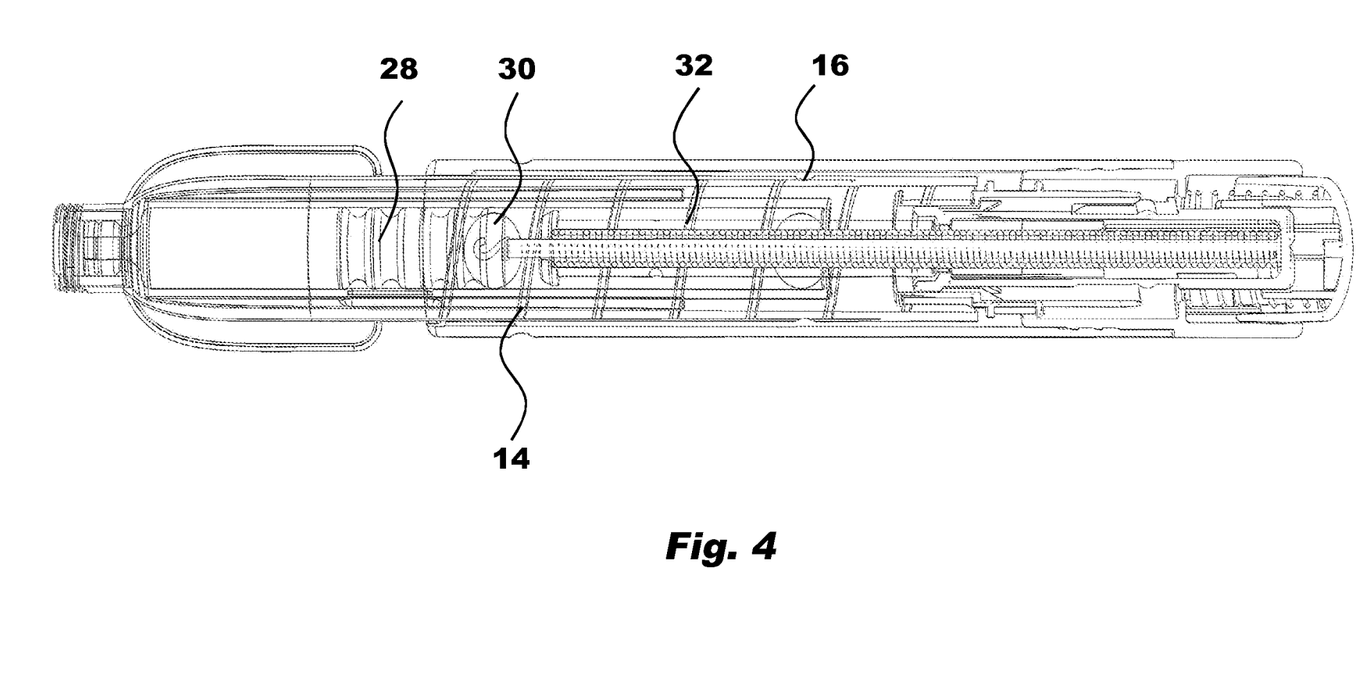
Figure 5:
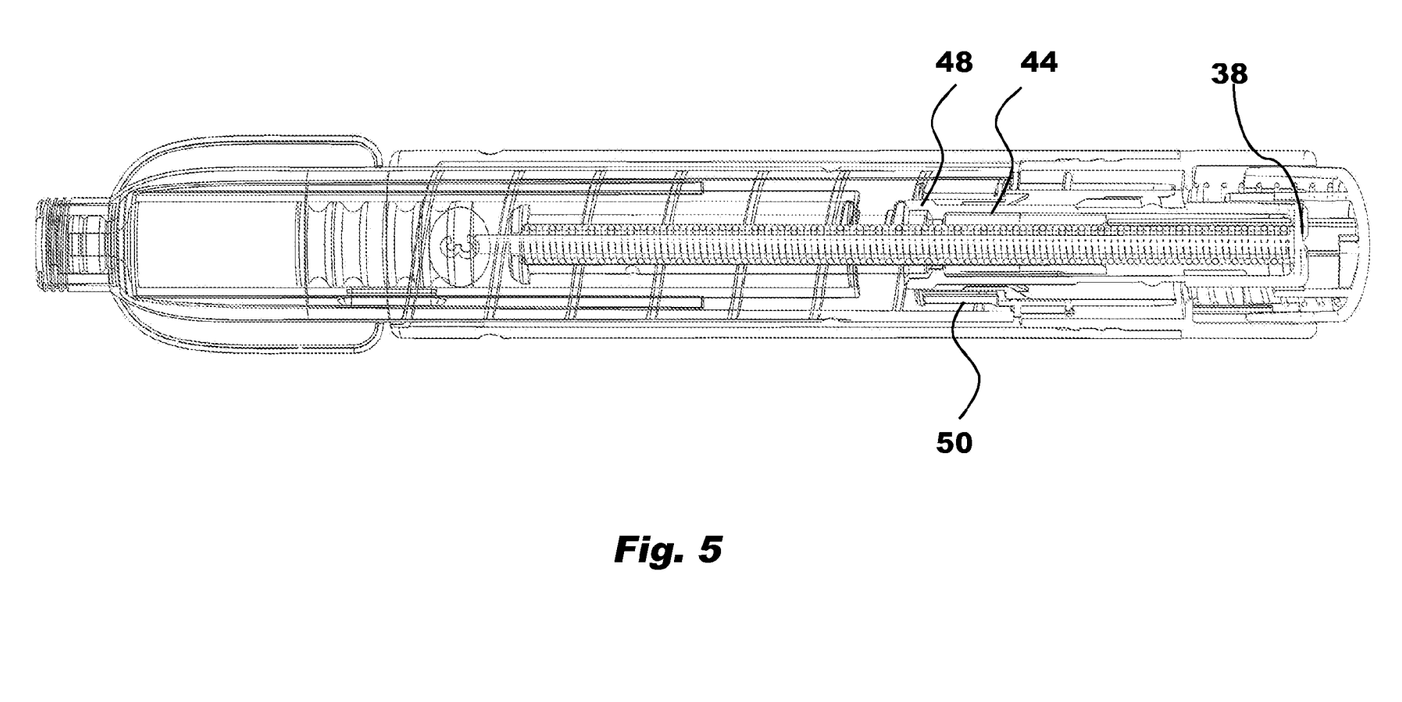
Figure 6:
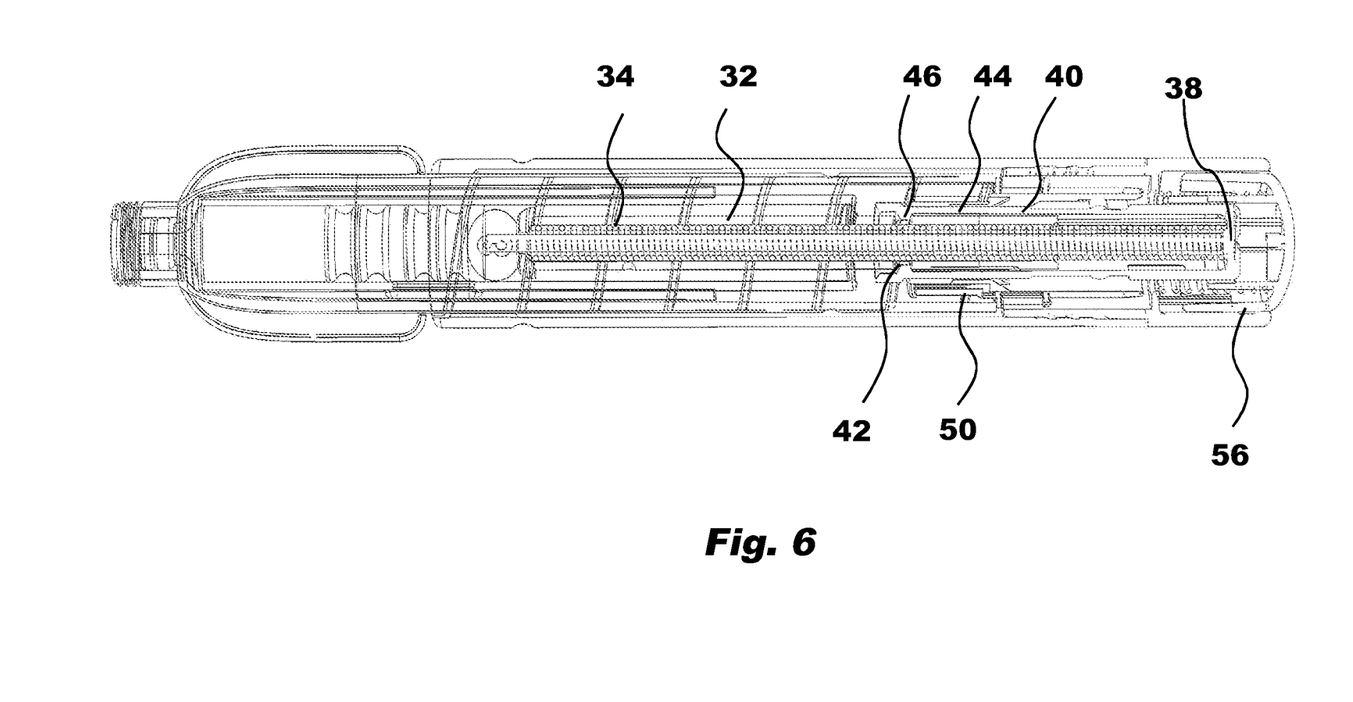

In the exemplary embodiment, the multi-chamber medicament container 22 is e.g. a dual chamber container designed with two compartments 24, 26 wherein one compartment contains preferably the medicament in powder form and the other compartment contains preferably a diluent, FIG. 2. The two compartments are separated by a resilient, movable stopper 28, which stopper when moved, opens passages between the compartments for mixing the medicament with the diluent. A distally arranged second stopper 30 closes the distal end of the medicament container.

The drive force mechanism in the exemplary embodiment comprises a drive force spring 34, an elongated plunger rod 32 and a drive member 40, wherein said drive member is coaxially arranged on the plunger rod and partially surrounding said plunger rod. The elongated plunger rod 32 has a proximal end in contact with the distal stopper 30. Inside the plunger rod 32 is arranged the drive force spring 34, between a proximal end wall 36 of the plunger rod 32 and a distal end wall 38 of the drive member 40, FIG. 2.

In the exemplary embodiment, the drive member 40 has a generally tubular shape. The outer surface of the distal tubular part of the drive member 40 comprises an annular ledge which is arranged to abut the circumferential ledge on the inner surface of the distal housing part when a part of the distal tubular part of the drive member passes through the aperture formed by the circumferential ledge on the inner surface of the distal housing part. The releasable means 44 of the drive member 40 are longitudinally extending and radially flexing arms provided with inwardly extending ledges 46 and the counter releasable means 42 of the plunger rod 32 is a groove on its circumferential outer surface, wherein the inwardly extending ledges 46 fit into said groove. Preferably said longitudinally extending and radially flexing arms are configured to exert a radial outwardly directed force. Each arm 44 is further arranged with an outwardly directed ledge 48.

The holding member 50 in the exemplary embodiment has a generally tubular shape and is coaxially arranged over the drive member 40. The holding member is in an inactive position when the holding member is completely surrounding the radially flexing arms i.e. the ledges 48 of the arms 44 are completely surrounded by the inner surface of the holding member 50. The holding member 50 is axially movable in relation to the distal housing part, preferably arranged to be axially moved in relation to the distal housing part a predetermined distance towards a distal end of the device by the proximal housing part when said housing parts are moved towards each other. In other words, the holding member 50 is slidably moved from the inactive position towards the distal end of the device to an active position wherein the holding member partially surrounds the radially flexing arms i.e. the ledges 48 of the arms 44 are partially surrounded by the inner surface of the holding member 50. The drive member 40 is further arranged with outwardly extending bumps or protrusions 54 on its outer circumferential surface for holding the holding member 50 in position relative the drive member 40, preventing the holding member 50 from sliding in relation to the drive member 40 when the holding member is in the inactive position.

The drive force mechanism is in a loaded state when the drive force spring 34 is pre-tensioned within said plunger rod, when the drive member is engaged to the plunger rod and when the holding member is either in the inactive or active position.

The actuation member 56 is in the form of a sleeve, preferably as a push button in the exemplary embodiment and comprises a touchable part that protrudes from the distal housing part 10. Preferably, a distal part of the actuation member protrudes from the distal end of the distal housing part. The actuation member is preferably movable in relation to distal housing part in a longitudinal direction along the longitudinal axis of the device. The actuation member 56 is provided with an inner sleeve extending along the longitudinal axis of the device and into which a portion of the distal tubular part of the drive member 40 fits. However, the drive member is preferably fixedly connected to the actuation member. Preferably, there is a certain distance between the distal end wall of the drive member 40 and a transversal wall of the actuation member 56. The actuation member 56 is resiliently connected to the distal housing part such that after each time the actuation member is biased it will recoil. Thus, a resilient member 58 is arranged between the transversal wall of the actuation member 56 and the circumferential ledge on the inner surface of the distal housing part. Therefore, the actuation member can be biased in relation to the distal housing part from a non-operating position in which the actuation member partially protrudes from the distal housing part to an operating position in which the actuation member is confined within the distal housing and will always recoil after being biased.

In the exemplary embodiment, the engagement means of the actuation member 56 are proximally extending tongues 52 and the counter engagements means 33 is a distal end annular surface of the plunger rod 32. Preferably, the proximally extending tongues 52 extend through apertures arranged on the distal end wall 38 of the drive member 40.

In the exemplary embodiment, the co-acting means 60 of the proximal housing part 12 is its distal end annular surface and the counter co-acting means 62 of the holding member 50 is an annular ledge on the proximal outer circumference of the holding member.

The device of the exemplary embodiment is intended to function as follows. When the device is delivered to a user the proximal housing part 12 is extended in relation to the distal housing part 10, FIG. 1. First the user attaches a medicament delivery member (not shown) to the proximal neck portion 18 of the proximal housing part 12. The next step is then to mix the components in the multi-chamber medicament container 22. The user then turns the proximal housing part 12 in relation to the distal housing part 10, whereby the proximal housing part is moved or retracted into the distal housing part. This relative movement of the two housing parts causes the plunger rod 32 to move in relation to the medicament container 22 such that its proximal end pushes the distal stopper 30 in the proximal direction. This in turn causes the resilient movable proximal stopper 28 to move such that passages are opened between the two compartments and the mixing is performed, FIG. 4.

Before mixing the components within the container, the actuation member 56 is in the non-operating position and the holding member 50 is in the inactive position. The inactive position of the holding member in the exemplary embodiment is characterized by the position of the holding member 50 when it is completely surrounding the radially flexing arms 44 of the drive member 40 such that the inwardly directed ledge 46 of the arms 44 are held in the groove 42 of the plunger rod 32 and thereby the drive force spring 34 is held pre-tensioned within the plunger rod 32, i.e. the drive force mechanism is in the loaded state. Further, when the holding member is in the inactive position and in the case that the actuation member 56 is biased from the non-operating position to the operating position, the resilient member 58 is compressed, the drive force mechanism and the holding member 50 are moved towards the proximal end of the device due to the engagement between the actuation member 56 and the plunger rod 32 by the engagement 52 and counter engagement 33 means and due to the engagement between the plunger rod and the drive member 40 by the inwardly directed ledge 46 of the arms 44 of the drive member and the groove of the plunger rod. However, it is not possible to activate the device prior to mixing, i.e. it is not possible to release the drive force mechanism from its loaded state. Moreover, the actuation member is recoiled.

When the mixing is about to be completed, the distal end annular surface 60 of the proximal housing part 12 is moved into contact with the annular ledge 62 on the outer circumference of the holding member 50 such that the holding member is moved from the inactive position to the active position. Then, the holding member is held fixed between the circumferential ledge on the inner surface of the distal housing part and the distal annular ledge of the proximal housing part. The active position of the holding member in the exemplary embodiment is characterized by the position of the holding member 50 when it is positioned in relation to the drive member such that a part of the ledges 48 of the arms 44 protrude out of the proximal end of the holding member 50, FIG. 5, i.e. the ledges 48 of the arms 44 are partially surrounded by the inner surface of the holding member 50.

The next step is now to perform a dose delivery. The user then positions the proximal part of the device at the medicament delivery site. When an injection needle is used, the device is pressed on a skin surface of the patient, whereby a penetration of the needle is performed.

Figure 7:
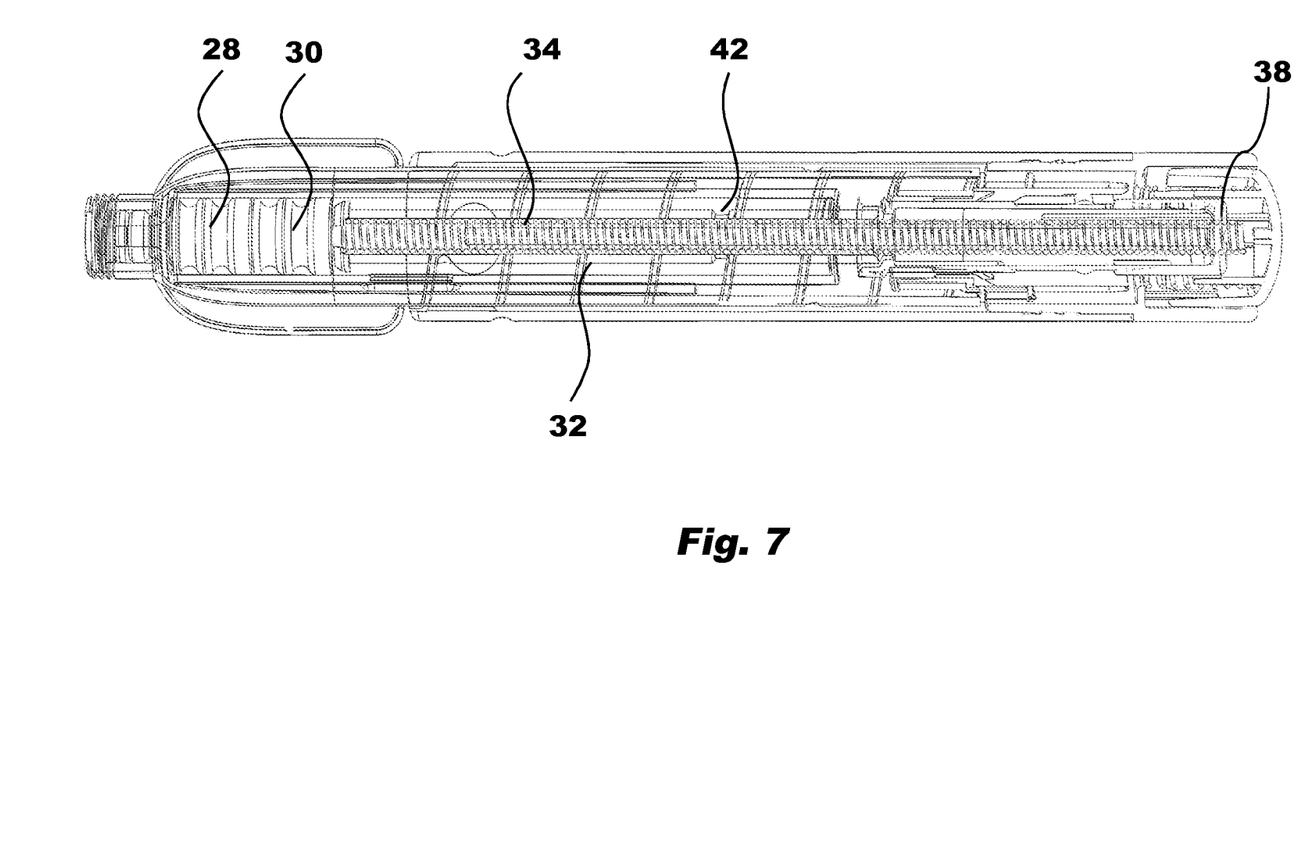

After this the actuation member, i.e. the push button 56 is biased, FIG. 7. This causes the resilient member 58 to be compressed, the plunger rod 32 to be moved towards the proximal end of the device together with the drive member 40 until the ledges 48 of the arms 44 have passed completely the proximal end of the holding member 50. The arms 44 of the drive member 40 are thereby free to expand in the radial outward direction whereby the inwardly directed ledges 46 move out of the groove 42 of the plunger rod 32. The latter is now free to move in the proximal direction by the force of the drive spring 34, which causes the stoppers 28, 30 of the medicament container 22 to be moved in the proximal direction, thereby expelling a dose of medicament through the medicament delivery member, FIG. 7. Also, due to the movement of the drive member towards the proximal end of the device, a gap is created between the annular ledge on the outer surface of the distal tubular part of the drive member and the circumferential ledge on the inner surface of the distal housing part.

Figure 8:
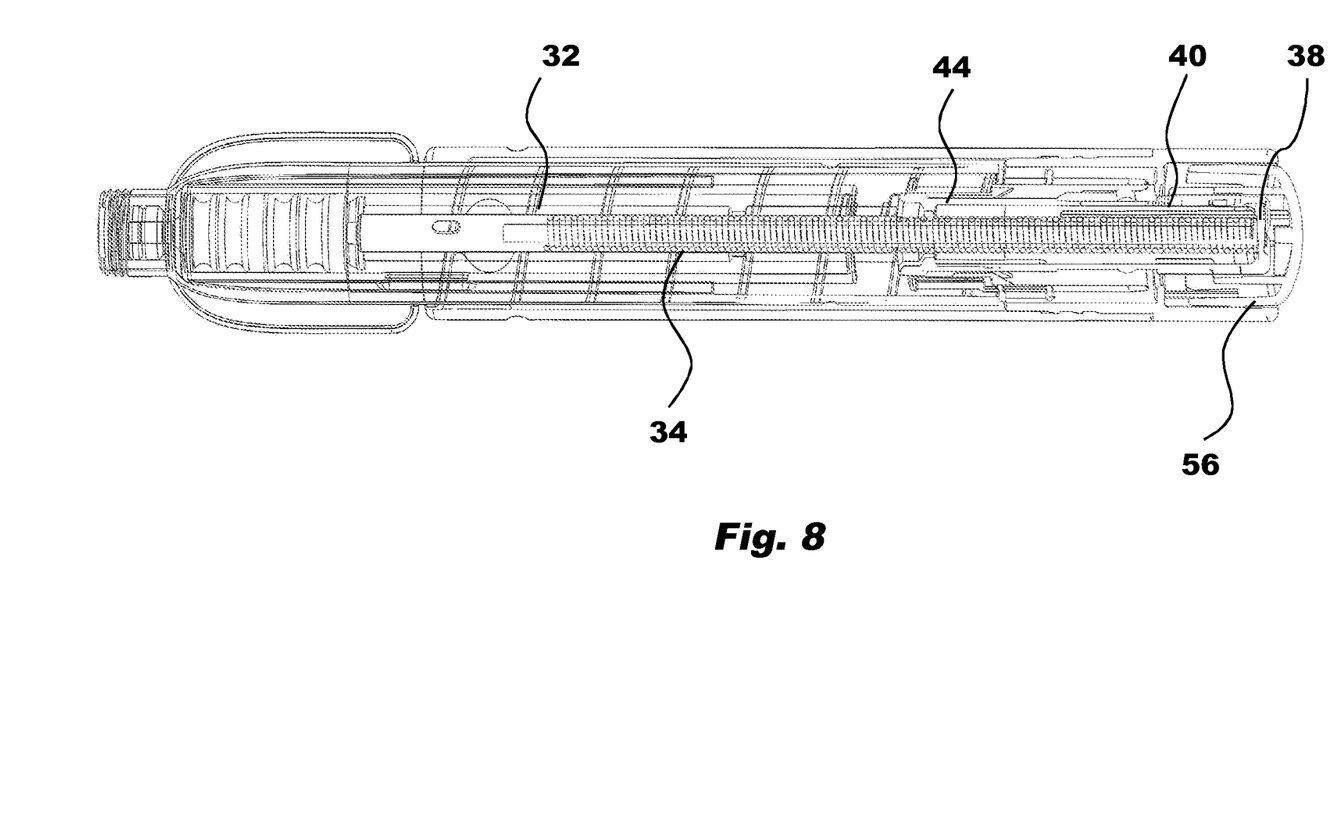

At the end of the injection sequence, the distal end of the plunger rod 32 passes the proximal end of the drive member 40, FIG. 8. The arms 44 of the drive member 40 are then free to move radially inwards inside the holding member 50 and due to the residual force of the drive spring 34, the drive member 40 will be pushed in the distal direction until the annular ledge on the outer surface of the distal tubular part of the drive member hits the circumferential ledge on the inner surface of the distal housing part. This contact provides an audible sound, like a click, as well as a tactile feeling of the actuation member, which indicates the end of delivery. The actuation member is also recoiled. If the user is still depressing the actuation member, the user will be provided with a tactile feedback that indicates the end of delivery.

When the medicament delivery operation has been completed, the device may be removed from the medicament delivery site and be discarded in a safe way.

More preferably, the actuation member is always recoiled after the actuation member is biased regardless of whether the actuation mechanism is released.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
a generally elongated housing, comprises a proximal housing part and a distal housing part movable relative each other;
a drive force mechanism accommodated in the distal housing part and slidably arranged in relation to the distal housing part;
a container filled with medicament arranged within the proximal housing part;
a holding member operably connected to the drive force mechanism for holding the drive force mechanism in a loaded state and arranged to be axially moved in relation to the distal housing part a predetermined distance toward a distal end of the device by the proximal housing part when the proximal and distal housing parts are moved toward each other; and
an actuation member configured to be biased in relation to the distal housing part from a non-operating position, in which the actuation member partially protrudes from the distal housing part, to an operating position, in which the actuation member is confined within the distal housing part;
wherein the actuation member is operably connected to the drive force mechanism for releasing the drive force mechanism from the loaded state; the actuation member is resiliently connected to the distal housing part such that the actuation member is always recoiled after being biased regardless of whether the actuation mechanism is released; and the drive force mechanism is configured to be released from the loaded state only after the holding member axially moves in relation to the distal housing part and the actuation member is biased from the non-operating position to the operating position.

2. The medicament delivery device of claim 1, wherein the drive force mechanism comprises a plunger rod, a drive force spring, and a drive member.

3. The medicament delivery device of claim 2, wherein the actuation member comprises an engagement device and the plunger rod comprises a counter-engagement device that interact together and configured such that the plunger rod is axially moved the predetermined distance in relation to the distal housing part when the actuation member is biased.

4. The medicament delivery device of claim 3, wherein the drive member comprises a releasable device and the plunger rod comprises a counter-releasable device that interact together for releasably engaging the plunger rod to the drive member.

5. The medicament delivery device of claim 4, wherein the releasable device of the drive member includes radially flexing arms provided with inwardly extending ledges, and the counter-releasable device of the plunger rod includes a groove on its circumferential outer surface; the inwardly extending ledges fit into the groove; and the holding member completely surrounds the radially flexing arms when the holding member is in an inactive position.

6. The medicament delivery device of claim 5, wherein the holding member is arranged to be axially moved in relation to the distal housing part a predetermined distance toward the distal end of the device from the inactive position to an active position, in which the holding member partially surrounds the radially flexing arms.

7. The medicament delivery device of claim 6, wherein the active position of the holding member corresponds to a position of the multi-chamber, in which the multi-chamber is mixed.

8. The medicament delivery device of claim 1, wherein the engagement device includes proximally extending tongues of the actuation member, and the counter-engagement device includes a distal-end annular surface of the plunger rod.

9. The medicament delivery device of claim 1, wherein the container is a multi-chamber medicament container, and the materials in the multi-chamber are mixed by moving the proximal and distal housing part in toward each other.

10. The medicament delivery device of claim 1, wherein the proximal housing part comprises a co-acting device and the holding member comprises a counter co-acting device that interact together for moving the holding member in relation to the distal housing part the predetermined distance toward the distal end of the device.

11. The medicament delivery device of claim 10, wherein the drive force mechanism comprises a plunger rod, a drive force spring, and a drive member.

12. The medicament delivery device of claim 11, wherein the actuation member comprises an engagement device and the plunger rod comprises a counter-engagement device that interact together and configured such that the plunger rod is axially moved the predetermined distance in relation to the distal housing part when the actuation member is biased.

13. The medicament delivery device of claim 12, wherein the drive member comprises a releasable device and the plunger rod comprises a counter-releasable device that interact together for releasably engaging the plunger rod to the drive member.

14. The medicament delivery device of claim 13, wherein the releasable device of the drive member includes radially flexing arms provided with inwardly extending ledges, and the counter-releasable device of the plunger rod includes a groove on its circumferential outer surface; the inwardly extending ledges fit into the groove; and the holding member completely surrounds the radially flexing arms when the holding member is in an inactive position.

15. The medicament delivery device of claim 14, wherein the holding member is arranged to be axially moved in relation to the distal housing part a predetermined distance toward the distal end of the device from the inactive position to an active position, in which the holding member partially surrounds the radially flexing arms.

16. The medicament delivery device of claim 15, wherein the container is a multi-chamber medicament container, and the materials in the multi-chamber are mixed by moving the proximal and distal housing part in toward each other.

17. The medicament delivery device of claim 16, wherein the active position of the holding member corresponds to a position of the multi-chamber, in which the multi-chamber is mixed.

18. The medicament delivery device of claim 10, wherein the engagement device includes proximally extending tongues of the actuation member, and the counter-engagement device includes a distal-end annular surface of the plunger rod.

* * * * *